US012558089B2

(12) United States Patent
Dumanian

(10) Patent No.: US 12,558,089 B2
(45) **Date of Patent: *Feb. 24, 2026**

(54) INDIRECT ATTACHMENT OF A NEEDLE TO A MESH SUTURE

(71) Applicant: Northwestern University, Evanston, IL (US)

(72) Inventor: Gregory A. Dumanian, Chicago, IL (US)

(73) Assignee: Northwestern University, Evanston, IL (US)

( * ) Notice: Subject to any disclaimer, the term of this patent is extended or adjusted under 35 U.S.C. 154(b) by 145 days.

This patent is subject to a terminal disclaimer.

(21) Appl. No.: 18/397,177

(22) Filed: Dec. 27, 2023

(65) Prior Publication Data

US 2024/0245399 A1     Jul. 25, 2024

Related U.S. Application Data

(63) Continuation of application No. 17/371,779, filed on Jul. 9, 2021, now Pat. No. 11,890,003, which is a
(Continued)

(51) Int. Cl.
*A61B 17/06* (2006.01)
*A61L 17/00* (2006.01)
(Continued)

(52) U.S. Cl.
CPC ........ *A61B 17/06166* (2013.01); *A61B 17/06* (2013.01); *A61L 17/00* (2013.01);
(Continued)

(58) Field of Classification Search
CPC ... A61B 17/06; A61B 17/06166; A61B 17/04; A61B 17/12; A61B 17/14; A61B 2017/0608; A61B 2017/00526
See application file for complete search history.

(56) References Cited

U.S. PATENT DOCUMENTS 3,037,619 A     6/1962     Stevens
3,304,557 A     2/1967     Polansky
(Continued)

FOREIGN PATENT DOCUMENTS

CN     1547455     11/2004
CN     1652826 A     8/2005
(Continued)

OTHER PUBLICATIONS

Australian Exam Report in Application 2019275649, mailed Jun. 5, 2021, 4 pages.
(Continued)

*Primary Examiner* — Vi X Nguyen
(74) *Attorney, Agent, or Firm* — Merchant & Gould P.C.

(57)     ABSTRACT

A medical device includes a surgical needle, an elongated suture, and an intervening segment. The elongated suture has a first end proximate to the needle and a second end located away from the needle. The elongated suture also includes a plurality of fibers defining a mesh wall between the first and second ends. A plurality of pores extend through the mesh wall, at least some which are in the macroporous size range of greater than 200 microns for facilitating tissue integration when introduced into a body. The intervening segment is disposed between and connected to either or both ends of the elongated suture and the needle. The intervening segment includes one or more fibers of the plurality of fibers and has a cross-sectional dimension smaller than a cross-sectional dimension of the mesh wall such that the intervening segment facilitates indirect attachment of the elongated macroporous mesh suture to the needle.

14 Claims, 3 Drawing Sheets

Related U.S. Application Data continuation of application No. 16/291,498, filed on Mar. 4, 2019, now Pat. No. 11,064,996, which is a continuation of application No. 15/825,960, filed on Nov. 29, 2017, now Pat. No. 10,278,694, which is a continuation-in-part of application No. 15/556,831, filed as application No. PCT/US2016/020231 on Mar. 1, 2016, now abandoned, said application No. 15/825, 960 is a continuation-in-part of application No. 14/976,864, filed on Dec. 21, 2015, which is a continuation of application No. 13/713,665, filed on Dec. 13, 2012, now Pat. No. 9,237,889.

(60) Provisional application No. 62/134,099, filed on Mar. 17, 2015, provisional application No. 61/602,183, filed on Feb. 23, 2012.

(51) Int. Cl.

| | |
|---|---|
| *A61L 17/04* | (2006.01) |
| *A61L 17/12* | (2006.01) |
| *A61L 17/14* | (2006.01) |
| *A61B 17/00* | (2006.01) |
| *A61B 17/04* | (2006.01) |

(52) U.S. Cl.
CPC .............. *A61L 17/04* (2013.01); *A61L 17/12* (2013.01); *A61L 17/145* (2013.01); *A61B 2017/00526* (2013.01); *A61B 2017/0412* (2013.01); *A61B 2017/0417* (2013.01); *A61B 2017/0461* (2013.01); *A61B 2017/0464* (2013.01); *A61B 2017/06009* (2013.01); *A61B 2017/0608* (2013.01); *A61B 2017/061* (2013.01); *A61B 2017/06185* (2013.01); *Y10T 29/49826* (2015.01)

(56) References Cited

U.S. PATENT DOCUMENTS

| | | | |
|---|---|---|---|
| 3,316,557 | A | 5/1967 | Liebig |
| 3,514,791 | A | 6/1970 | Sparks |
| 3,918,455 | A | 11/1975 | Coplan |
| 4,034,763 | A | 7/1977 | Frazier |
| 4,372,293 | A * | 2/1983 | Vijil-Rosales ......... A61B 17/06 |
| | | | 623/7 |
| 4,392,495 | A | 7/1983 | Bayers |
| 4,510,934 | A | 4/1985 | Batra |
| 4,712,553 | A | 12/1987 | MacGregor |
| 4,880,002 | A | 11/1989 | MacGregor |
| 5,280,674 | A | 1/1994 | Granger |
| 5,382,257 | A | 1/1995 | Lewis |
| 5,423,821 | A | 6/1995 | Pasque |
| 5,450,860 | A | 9/1995 | O'Connor |
| 5,645,568 | A | 7/1997 | Chervitz |
| 5,879,371 | A | 3/1999 | Gardiner |
| 5,899,909 | A | 5/1999 | Claren |
| 5,984,333 | A | 11/1999 | Constantijn |
| 5,984,933 | A | 11/1999 | Yoon |
| 6,143,029 | A | 11/2000 | Rippstein |
| 6,296,659 | B1 | 10/2001 | Foerster |
| 6,315,788 | B1 | 11/2001 | Roby |
| 6,406,423 | B1 | 6/2002 | Scetbon |
| 6,475,139 | B1 | 11/2002 | Miller |
| 6,478,727 | B2 | 11/2002 | Sctebon |
| 6,620,185 | B1 | 9/2003 | Harvie |
| 6,638,211 | B2 | 10/2003 | Suslian |
| 6,814,741 | B2 | 11/2004 | Bowman |
| 6,911,003 | B2 | 6/2005 | Anderson |
| 6,981,944 | B2 | 1/2006 | Jamiolkowski |
| 7,481,826 | B2 | 1/2009 | Cichocki |
| 7,547,316 | B2 | 6/2009 | Priewe |
| 7,582,105 | B2 | 9/2009 | Kolster |
| 7,621,864 | B2 | 11/2009 | Suslian |
| 7,658,751 | B2 | 2/2010 | Stone |
| 7,740,646 | B2 | 6/2010 | Hunt |
| 7,815,562 | B2 | 10/2010 | Chu |
| 7,875,055 | B2 | 1/2011 | Cichocki |
| 8,047,982 | B2 | 11/2011 | Kammerer |
| 8,062,363 | B2 | 11/2011 | Hirpata |
| 8,128,656 | B2 | 3/2012 | Cichocki |
| 8,202,306 | B2 | 6/2012 | Dreyfuss |
| 8,257,393 | B2 | 9/2012 | Cichocki |
| 8,273,011 | B2 | 9/2012 | Browning |
| 8,298,247 | B2 | 10/2012 | Sterret |
| 8,574,149 | B2 | 11/2013 | Evans |
| 8,613,755 | B1 | 12/2013 | Foerster |
| 9,237,889 | B2 | 1/2016 | Dumanian |
| 10,278,694 | B2 | 5/2019 | Dumanian |
| 10,500,031 | B2 | 12/2019 | Levinson |
| 11,064,996 | B2 | 7/2021 | Dumanian |
| 11,351,022 | B2 | 6/2022 | Levinson |
| 11,426,267 | B2 | 8/2022 | Levinson |
| 2002/0107430 | A1 | 8/2002 | Neisz |
| 2003/0050530 | A1 | 3/2003 | Neisz |
| 2003/0149447 | A1 | 8/2003 | Morency |
| 2004/0054253 | A1 | 3/2004 | Snitkin |
| 2004/0144394 | A1 | 7/2004 | Dauner |
| 2004/0162579 | A1 | 8/2004 | Foerster |
| 2005/0028304 | A1 | 2/2005 | Becker |
| 2005/0119696 | A1 | 6/2005 | Walters |
| 2005/0171569 | A1 | 8/2005 | Girard et al. |
| 2005/0192631 | A1 | 9/2005 | Grafton |
| 2005/0277985 | A1 | 12/2005 | Wert |
| 2005/0283040 | A1 | 12/2005 | Greenhalgh |
| 2006/0229675 | A1 | 10/2006 | Novoa |
| 2007/0068538 | A1 | 3/2007 | Anderson |
| 2008/0034801 | A1 * | 2/2008 | Canham ........... A61F 13/00051 |
| | | | 65/444 |
| 2008/0051833 | A1 | 2/2008 | Gramuglia |
| 2008/0082113 | A1 | 4/2008 | Bishop |
| 2008/0119880 | A1 | 5/2008 | Chu |
| 2008/0132943 | A1 | 6/2008 | Maiorino et al. |
| 2008/0140123 | A1 | 6/2008 | Ferree |
| 2008/0207989 | A1 | 8/2008 | Kaleta |
| 2008/0281355 | A1 | 11/2008 | Mayer |
| 2008/0294193 | A1 | 11/2008 | Schwartz |
| 2009/0012560 | A1 | 1/2009 | Hunter |
| 2009/0112258 | A1 | 4/2009 | Kreidler |
| 2009/0182375 | A1 | 7/2009 | Isse |
| 2009/0192347 | A1 | 7/2009 | Davila |
| 2009/0216326 | A1 | 8/2009 | Hirpata |
| 2009/0228021 | A1 | 9/2009 | Leung |
| 2009/0248067 | A1 | 10/2009 | Maiorino |
| 2009/0248071 | A1 | 10/2009 | Saint |
| 2009/0318962 | A1 | 12/2009 | Spedden |
| 2010/0005685 | A1 | 1/2010 | Russell |
| 2010/0056857 | A1 | 3/2010 | Nordmeyer |
| 2010/0063599 | A1 | 3/2010 | Brunelle |
| 2010/0137679 | A1 | 6/2010 | Lashinski et al. |
| 2010/0241141 | A1 | 9/2010 | Lee |
| 2011/0010803 | A1 | 1/2011 | Zank |
| 2011/0046669 | A1 | 2/2011 | Goraltchouk |
| 2011/0054524 | A1 | 3/2011 | Beevers |
| 2011/0106153 | A1 | 5/2011 | Stone |
| 2011/0108039 | A1 | 5/2011 | Frigstad |
| 2011/0137419 | A1 | 6/2011 | Wong |
| 2011/0282384 | A1 | 11/2011 | Odermatt |
| 2011/0319932 | A1 | 12/2011 | Avelar |
| 2012/0065732 | A1 | 3/2012 | Roller |
| 2012/0083649 | A1 | 4/2012 | Suslian |
| 2012/0136388 | A1 | 5/2012 | Odermatt |
| 2012/0215063 | A1 | 8/2012 | Holsten et al. |
| 2012/0245629 | A1 | 9/2012 | Gross |
| 2013/0178699 | A1 | 7/2013 | Saint |
| 2013/0226232 | A1 * | 8/2013 | Dumanian .............. A61L 17/00 |
| | | | 606/224 |
| 2015/0362669 | A1 | 12/2015 | Aizenberg et al. |
| 2016/0106423 | A1 | 4/2016 | Dumanian |
| 2016/0166727 | A1 | 6/2016 | Ganatra et al. |
| 2018/0000480 | A1 | 1/2018 | Dumanian |
| 2018/0021040 | A1 | 1/2018 | Dumanian |
| 2018/0042608 | A1 | 2/2018 | Dumanian |

(56) References Cited

U.S. PATENT DOCUMENTS

| | | | |
|---|---|---|---|
| 2018/0078255 A1 | 3/2018 | Dumanian |
| 2018/0360453 A1 | 12/2018 | Dumanian |
| 2019/0192142 A1 | 6/2019 | Dumanian |
| 2020/0129172 A1 | 4/2020 | Dumanian |
| 2022/0054127 A1 | 2/2022 | Dumanian |
| 2022/0330939 A1 | 10/2022 | Dumanian |

FOREIGN PATENT DOCUMENTS

| | | | |
|---|---|---|---|
| CN | 101028204 A | 9/2007 |
| CN | 200980691 | 11/2007 |
| CN | 101219066 | 7/2008 |
| CN | 101321498 | 12/2008 |
| CN | 101380484 | 3/2009 |
| CN | 101401735 | 4/2009 |
| CN | 101431947 A | 5/2009 |
| CN | 101500495 | 8/2009 |
| CN | 201691977 | 1/2011 |
| CN | 201759610 | 3/2011 |
| CN | 102076280 A | 5/2011 |
| CN | 102076580 A | 5/2011 |
| CN | 202051754 | 11/2011 |
| CN | 103068323 A | 4/2013 |
| CN | 104168840 A | 11/2014 |
| CN | 104224253 A | 12/2014 |
| CN | 104274221 A | 1/2015 |
| CN | 204600572 U | 9/2015 |
| CN | 107405145 A | 11/2017 |
| EP | 490143 | 6/1992 |
| EP | 0887045 | 12/1998 |
| EP | 1060714 | 12/2000 |
| EP | 1541181 | 6/2005 |
| EP | 1844735 | 10/2007 |
| EP | 2774579 | 9/2014 |
| EP | 2816961 | 12/2014 |
| EP | 3410835 | 12/2018 |
| GB | 2458878 | 10/2009 |
| GB | 2464952 A | 5/2010 |
| GB | 2468307 A | 9/2010 |
| JP | 2003501144 A | 1/2003 |
| JP | 2003-523786 | 8/2003 |
| JP | 2006025867 A | 2/2006 |
| JP | 2011525411 A | 9/2011 |
| JP | 2015-501186 | 1/2015 |
| JP | 2015511160 A | 4/2015 |
| JP | 2017-213397 | 12/2017 |
| KR | 20100030009 A | 3/2010 |
| KR | 1020190006031 | 12/2012 |
| KR | 1020200006191 | 1/2020 |
| WO | 199617544 | 6/1996 |
| WO | 2000074613 | 12/2000 |
| WO | 02/087610 | 11/2002 |
| WO | 2003022161 | 3/2003 |
| WO | 2003092727 | 11/2003 |
| WO | 2004030517 | 4/2004 |
| WO | 2005007019 | 1/2005 |
| WO | 2006084165 | 8/2006 |
| WO | 2010008815 | 1/2010 |
| WO | 2010028197 | 3/2010 |
| WO | 2010051506 | 5/2010 |
| WO | 2010/100488 | 9/2010 |
| WO | 2011022515 | 2/2011 |
| WO | 2011025760 | 3/2011 |
| WO | 2013/126130 A1 | 8/2013 |
| WO | 2016/037065 | 3/2016 |
| WO | 2016148904 | 9/2016 |

OTHER PUBLICATIONS

Brazilian Office Action in Application BR122020002815-7, mailed Mar. 8, 2021, 4 pages.
Chinese Notice of Allowance in Application 201811129989.0, mailed May 17, 2021, 5 pages.
Dictionary.com, LLC, Tube Definition, accessed Jul. 13, 2020 at https://www.dictionary.com/browse/tube (Year: 2020).
DuBay et al., "Incisional herniation induces decreased abdominal wall compliance via oblique muscle atrophy and fibrosis," Ann Surg. Jan. 2007;245(1):140-146.
Indian Office Action in Application 7879/DELNP/2014, mailed Jun. 1, 2021, 6 pages.
Mesh Definition, Dictionary. com unabridged, Random House Unabridged Dictionary, Random House, Inc., accessed Oct. 21, 2020 from www.dictionary.com/browse/mesh (Year 2020).
Mexican Office Action in Application MX/2020/079934, mailed Feb. 15, 2021, 4 pages.
PCT International Application No. PCT/US2019/030109, International Search Report and Written Opinion, mailed Aug. 16, 2019, 14 pages.
PCT International Preliminary Report on Patentability in Application PCT/US2019/030109, mailed May 14, 2021, 10 pages.
PCT International Search Report and Written Opinion of the International Searching Authority for Application No. PCT/US2016/020231, mailed May 23, 2016.
Pore Definition, Mirriam-Webster.com Dictionary, accessed Oct. 21, 2020 from merriam-webster.com/dictionary/pore (Year 2020).
Schachtrupp, A., et al., "An implantable sensor device measuring suture tension dynamics: results of development and experimental work", Hernia 2016; 20: p. 601-606.
Anderson, Biological responses to materials, Ann. Rev. Mater. Res., 31:81-110 (2001).
Anderson, Inflammation, Wound Healing, and the Foreign-Body Response. Chapter 11.2.2, pp. 503-513, IN: Ratner et al. (eds.), Biomaterials Science, an Introduction to Materials in Medicine, 3rd., Elsevier (2013).
Armaiianzas, et al., "Prophylactic Mesh vs Suture in the Closure of the Umbilical Trocar Site after Laparoscopic Cholecystectomy in High-Risk Patients for Incisional Hernia. A Randomized Clinical Trial", ISSN 1072-7515/14, The American College of Surgeons, vol. 218, No. 5, May 2014.
Australian Office Action in Application 2019219868, mailed Nov. 3, 2020, 4 pages.
Australian Patent Application No. 2016233740, Examination Report No. 1, Nov. 1, 2019.
Australian Patent Application No. 2017261502, Examination Report No. 1, dated Dec. 12, 2018.
Bellon et al., Effect of relaparotomy through previously integrated polypropylene and polytetrafluoroethylene experimental implants in the abdominal wall, J. Am. Coll. Surg., 188:466-72 (1999).
Bellon et al., Integration of biomaterials implanted into abdominal wall: process of scar formation and macrophaae response, Biomaterials, 15:381-7 (1995).
Berger et al., Healing of arterial prostheses in man: its incompleteness, Ann. Surg., 175:118-27.
Bevoni, et al., "Long term results of acute achilles repair with triple-bundle technique and early rehabilitation protocol", Injury, Int. J. Care Injured 45 (2014) 1268-1274.
Bobryshev et al., Colonisation of prosthetic grafts by immunocompetent cells in a sheep model, Cardiovascular Surgery, 9(2):166-76 (2001).
Brazilian Patent Application No. BR11201420564-7, Search Report, dated Nov. 5, 2019.
Brewster, Chapter 37, Prosthetic Grafts, pp. 559-578 In: Rutherford, Vascular Surgery, Philadelphia: Saunders Co. (1995).
Brown et al., Which mesh for hernia repair, Ann. R. Coll. Surg. Engl., 92:272-8 (2010).
Burger, et al., "Incisional Hernia: Early Complication of Abdominal Surgery", World Journal of Surgery, (2005) 29: 1608-1613.
Canadian Patent Application No. 2865278, Office Action, dated Jul. 26, 2018.
Chinese Office Action, Chinese Application No. 201280070639.6, dated Feb. 26, 2016.
Chinese Patent Application No. 201680011861.7, First Office Action and Search Report, issued Oct. 16, 2019.
Chinese Patent Application No. 201880003637.2, First Office Action and Search Report, dated Sep. 18, 2019.
Chinese Patent Application No. 2022052101683730, First Office Action and Search Report, issued May 25, 2022, 16 pages.

(56) References Cited

OTHER PUBLICATIONS

Clowes et al., Mechanisms of arterial graft healing, Am. J. Pathol., 123:220-30 (1986).

Cobb et al., Textile analysis of heavy weight, mid-weight, and light weight polypropylene mesh in porcine ventral hernia model, J. Sura. Res., 136:1-7 (2006).

Conze et al., New polymer for intra-abdominal meshes—PVDF copolymer, J. Biomed. Mater. Res. Part B: Aoo. Biomater., 87B:321-8 (2008).

Conze et al., Polypropylene in the intra-abdominal position: influence of pore size and surface area, Hernia, 8:365-72 (2004).

Debakey et al., The fate of Dacron vascular grafts, Arch. Surg., 89:757-82 (1964).

Deeken et al., Physicomechanical evaluation of polypropylene, polyester, and polytetrafluoroethylene meshes for inguinal hernia repair, J. Am. Coll. Surg., 212:68-79 (2011).

Dirk Weyhe et al., "Large pore size and controlled mesh elongation are relevant predictors for mesh integration quality and low shrinkage—Systematic analysis of key parameters of meshes in a novel minipig hernia model", International Journal of Surgery, vol. 22, Oct. 1, 2015, pp. 46-53, XP055511014.

Dumanian et al., "Experimental Study of the Characteristics of a Novel Mesh Suture", British Journal of Surgery, Wiley Online Library, DOI: 10.1002/bis.9853, Apr. 8, 2015.

European Extended Search Report for European Application No. 17197004.9 dated Feb. 14, 2018.

European Patent Application No. 18155913.9, Extended European Search Report, dated Jun. 5, 2018.

European Patent Application No. 18742649.9, Communication Pursuant to Article 94(3) EPC, dated Jun. 7, 2019.

European Patent Application No. 18742649.9, Communication Pursuant to Article 94(3) EPC, dated Nov. 29, 2019.

Franz, The biology of hernia formation, Surg. Clin. N. Am., 88:1-15 (2008).

Golden et al., Healing of polytetrafluoroethylene arterial grafts is influenced by graft porosity, J. Vasc. Surg., 11:838-45 (1990).

Hake et al., Healing parameters of a new albumin-coated knitted Dacron graft, Thorac. Cardiovasc. Surgeon, 39:208-13 (1991).

Hore man et al., "Force Sensing in Surgical Sutures", PLOS One, vol. 8, Issue 12, Dec. 2013.

Houshang Seradge, M.D., "Elongation of the repair configuration following flexor tendon repair", The Journal of Hand Surgery, vol. 8, No. 2, 182-185, Mar. 1983.

Huang, et al., "Management of polypropylene mesh erosion after intravaginal midurethral sling operation for female stress urinary incontinence", International Urogynecologyy Journal, 437-440, 2005.

Israel Patent Application 269228, 2nd Office Action mailed May 31, 2020, 5 pages.

Israel Patent Application No. 234126, Office Action, dated Mar. 19, 2018.

Israel Patent Application No. 265173, Office Action, dated Sep. 9, 2019.

Japanese Office Action for Application No. JP 2014-558731, dated Feb. 7, 2017.

Japanese Office Action for Application No. JP 2017-148672, dated Aug. 31, 2018.

Japanese Patent Application No. 2017-547562, Notice of Reasons for Rejection, dated Sep. 3, 2019.

Japanese Patent Application No. 2019-511390, Office Action, Nov. 19, 2019.

Kaiser, Alloplastic replacement of canine trachea with Dacron, Thorac. Cardiovasc. Surg., 33:239-43 (1985).

Klinge et al., "The ideal mesh?", Pathobiology, 80: 169-75 (2013).

Klinge et al., Impact of polymer pore size on the interface scar formation in a rat model, J. Surg. Res., 103:208-14 (2002).

Klinge, et al., "Modified classification of surgical meshes for hernia repair based on teh analyses of 1,000 explanted meshes", Springerlink.com, Hernia (2012) 16:251-258, May 2012.

Ko et al., "Components Separation" technique for the treatment of complex abdominal wall defects: An 11-year experience with 200 patients, Arc. Surg., 144:1047-55 (2009).

Korean Notice of Allowance in Application 10-2019-7008610, mailed Jan. 30, 2020, 3 pages.

Korean Patent Application No. 10-2014-7026080, Office Action, dated Mar. 20, 2018.

Korean Patent Application No. 10-2019-7008610, Office Action, mailed Oct. 8, 2019.

Lista et al., Subglandular breast augmentation with textured, anatomic, cohesive silicone implants: a review of 440 consecutive patients, Plastic Reconstr. Surg., 132:295-303 (2013).

Mathisen et al., The influence of denier and porosity on performance of a warp-knit Dacron arterial prosthesis, Bob Hope International Heart Research Institute, vol. 203, No. 4, pp. 382-389 (1985).

McLeod et al., Does the size of the stitch length affect surgical site infection?, J. Am. Coll. Surg., pp. 556-560 (2013).

Mioton et al., "Theoretic and Evidence-based Laparotomy Closure with Sutures and Meshes", Plastic and Reconstructive Surgery, vol. 142, No. 3S, Sep. 2018.

Mo hi et al., "New Objective Measurement to Characterize the Porosity of Textile Implants", Journal of Biomedical Materials Research Part B: Applied Biomaterials DOI 10.1002/jbmb, p. 5 (Wiley Periodicals, Inc. 2007).

Morton, et al., "Urethral injury associated with minimally invasive mid-urethral sling procedures for the treatment of stress urinary incontinence: a case series and systematic literature search", The Authors Journal compilation, BJOG an International Journal of Obstetrics and Gynaecology, 1120-1126 2009.

Muhl et al., "New Objective Measurement to Characterize the Porosity of Textile Implants," Journal of Biomedical Materials Research Part B: Applied Biomaterials, Mar. 23, 2007, 8 pages.

Nakayama et al., In vivo tissue-engineered small-caliber arterial graft prosthesis consisting of autologous tissue (biotube), Cell Transplantation, 13:439-49 (2004).

Orenstein et al., Comparative analysis of histopathologic effects of synthetic meshes based on material, weight, and pore size in mice, J. Surg. Res., 176:423-9 (2012).

Pascual et al., Early tissue incorporation and collagen deposition in lightweight polypropylene meshes: bioassay in an experimental model of ventral hernia, Surgery, 144:427-35 (2008).

PCT International Preliminary Report on Patentability and Written Opinion for International Application No. PCT/US2016/020231, dated Sep. 19, 2017.

PCT International Preliminary Report on Patentability in Application PCT/US2018/039243, mailed Jun. 11, 2020, 12 pages.

PCT International Preliminary Report on Patentability, Written Opinion for Application No. PCT/US2012/069480 dated Sep. 4, 2014.

PCT International Search Report and Written Opinion for International Application No. PCT/US2018/039243, dated Oct. 10, 2018.

PCT International Search Report and Written Opinion of the International Searching Authority for Application No. PCT/US2016/020231, dated May 23, 2016.

PCT International Search Report for Application No. PCT/US2012/069480 dated Mar. 8, 2013.

PCT International Search Report for International Patent Application PCT/US2018/039243, dated Oct. 10, 2018.

PCT Written Opinion for Application No. PCT/US2012/069480 dated Mar. 8, 2013.

PCT Written Opinion for International Patent Application PCT/US2018/039243, dated Oct. 10, 2018.

Petter-Puchner AH, "The State of Midline Closure of the Abdominal Wall", British Journal of Surgery 102: 1446-1447, 2015.

Poulose et al., Epidemiology and cost of ventral hernia repair: making the case for hernia research, Hernia, 16:179-83 (2012).

Sauvage et al., Interspecies healing of porous arterial prostheses, Arch. Surg., pp. 698-705 (1974).

Smooth Breast Implants vs. Textured Breast Implants—Which should I choose?, downloaded from the Internet at <http://www.implantinfo.com/faqs/1.49.aspx> on Sep. 20, 2013.

Souza, M.D., et al., "In Vivo Evaluation of a Novel Mesh Suture Design for Abdominal Wall Closure", Division of Plastic Surgery,

(56)         References Cited

OTHER PUBLICATIONS

Northwestern University Feinberg School of Medicine, DOI: 10.1097/prs.0000000000000910, Apr. 11, 2014.
Sparks, Die-Grown reinforced arterial grafts: observations on long-term animal grafts and clinical experience, Ann. Surgery, pp. 787-794 (Nov. 1970).
Spear et al., Late seromas after breast implants: theory and practice, Plast. Reconstr. Surg., 130:423-35 (2012).
Sweat, et al., "Polypropylene Mesh Tape for Stress urinary Incontinence: Complications of Urethral Erosion and Outlet Obstruction", The Journal of Urology, vol. 168, 144-146, Jul. 2002.
Tsuchida et al., Healing mechanisms of PTFE grafts: significance of transmural structure, J. Surg. Res., 71:187-95 (1997).
Tsukada et al., Experimental study of a new tracheal prosthesis: pored Dacrob tube, J. Thorac. Cardiovasc. Surg., 127:877-84 (2004).
US Non-final Office Action for U.S. Appl. No. 15/825,960, dated Aug. 31, 2018.
U.S. Appl. No. 14/976,864, Nonfinal Office Action, dated Jun. 6, 2019.
U.S. Appl. No. 15/556,831, Nonfinal Office Action, dated Oct. 30, 2019.
U.S. Appl. No. 15/703,185, Nonfinal Office Action, dated Aug. 19, 2019.
U.S. Appl. No. 15/703,308, Nonfinal Office Action, dated Jul. 5, 2019.
Weslowski et al., Porosity: Primary determinant of ultimate fate of synthetic vascular grafts, Surgery, 50:91 (1961).
White, The effect of porosity and biomaterial on the healing and long-term mechanical properties of vascular prostheses, ASAIO Trans., 34:95-100 (1988).
Wilson, Vascular Access: Principles and Practice, 5th ed., pp. 65-68 (2010).
Xing et al., "Early laparotomy wound failure as the mechanism for incisional hernia formation", Journal of Surgical Research, www.sciencedirect.com, E35-E42, 2012.

* cited by examiner

INDIRECT ATTACHMENT OF A NEEDLE TO A MESH SUTURE

CROSS-REFERENCE TO RELATED APPLICATIONS

This application is a continuation of U.S. patent application Ser. No. 17/371,779, now U.S. Pat. No. 11,890,003, filed Jul. 9, 2021, which is a continuation of U.S. patent application Ser. No. 16/291,498, now U.S. Pat. No. 11,064, 996, filed Mar. 4, 2019, which is a continuation of U.S. patent application Ser. No. 15/825,960, now U.S. Pat. No. 10,278,694, filed Nov. 29, 2017, which is a continuation-in-part of U.S. patent application Ser. No. 14/976,864, filed Dec. 21, 2015, which is a continuation of U.S. patent application Ser. No. 13/713,665, now U.S. Pat. No. 9,237, 889, filed Dec. 13, 2012, which claims the priority benefit of U.S. Provisional Patent Application No. 61/602,183, filed Feb. 23, 2012. This is also a continuation-in-part of U.S. patent application Ser. No. 15/556,831, filed Sep. 8, 2017, which is a National Stage Application of PCT/US16/20231, filed Mar. 1, 2016, which claims the priority benefit of U.S. Provisional Patent Application No. 62/134,099, filed Mar. 17, 2015. The entire contents of each of the foregoing is expressly incorporated herein by reference.

FIELD OF THE DISCLOSURE

The present disclosure is directed to mesh sutures having structural characteristics that strengthen closure, prevent suture pull-through, and/or resist infection.

BACKGROUND

One of the foundations of surgery is the use of sutures to re-appose soft tissue, i.e., to hold tissue in a desired configuration until it can heal. In principle, suturing constitutes introducing a high tensile foreign construct (looped suture) into separate pieces of tissue in order to hold those pieces in close proximity until scar formation can occur, establishing continuity and strength between tissues. Sutures initially provide the full strength of the repair, but then become secondarily reinforcing or redundant as the tissue heals. The time until tissue healing reaches its maximal strength and is dependent on suture for approximation, therefore, is a period of marked susceptibility to failure of the repair due to forces naturally acting to pull the tissues apart.

Conventional sutures provide a circular or single-point cross-sectional profile extended over the length of the suture material. Such a suture has the great benefit of radial symmetry, which eliminates directional orientation, allowing the user (e.g., physician, surgeon, medic, etc.) to not have to worry about orienting the suture during use. However, a considerable disadvantage of conventional sutures with a single-point cross-section is that this construct cannot effectively distribute force, and instead, actively concentrates force at a geometric point (e.g., the point at the leading edge of the circle) creating a sharp edge in the axial dimension. Under these conditions, the tissue is continuously exposed to tension, increasing the likelihood that stress concentration at a geometric point or sharp edge will cut through the tissue.

More recently, as described in U.S. Pat. No. 9,237,889 (the entire contents of which are expressly incorporated herein by reference), Dr. Gregory Dumanian has invented a macroporous mesh suture that advantageously leverages the body's natural healing response to resist twice the magnitude of load as that of conventional sutures before pulling through. This macroporosity encourages tissue growth in, around, and through the entire suture.

For most applications, the size (e.g., diameter) of conventional sutures are less than 1 mm. It is common for needles to be directly attached to standard sutures, with a drilled hole creating an interval void at the end opposite the sharp tip. This drilled hole receives the first end of the suture to be directly attached. Alternatively, the suture is placed (i.e. swaged) onto a flat or v-shaped channel located at the end of the needle opposite the sharp tip, with the channel then being bent or crimped to achieve a direct attachment of the needle to the first end of the conventional suture.

Macroporous mesh sutures are much larger than conventional sutures. This creates a problem of needle attachment because the size of such macroporous mesh sutures range from 1 mm to 5 mm or more. Standard direct attachments via drill holes or channels at the end of the needle away from its sharp tip would require an introducing element or trocar far larger than a standard needle. Examples of a large introducing elements or trocars connected to macroporous meshes is in the art of gynecology slings and tapes. Far better, however, is for the introducing agent (needle) to be smaller than the macroporous mesh suture to minimize tissue trauma. Macroporous mesh sutures do not require a large hole, as the suture collapses during passage through tissue. A mesh suture directly attached to a needle that large would not only be difficult and cumbersome for the surgeon to use, the larger needle diameters required would unnecessarily create large holes in the tissue during use and therefore unnecessarily harm normal tissue during use. For this reason, a method of indirectly attaching a mesh suture to a standard sized needle is described herein. For example, to attach a mesh suture directly into a hole or channel in a conventional surgical needle, the hole, channel, and needle itself would need to be the same approximate size as the mesh suture. A mesh suture directly attached to a needle that large would not only be difficult and cumbersome for the surgeon to use, the larger needle diameters required would unnecessarily harm normal tissue during use. For this reason, a method of indirectly attaching a mesh suture to a standard sized needle is described herein.

GENERAL DESCRIPTION

The present disclosure is directed to a medical device including a novel structure for indirectly attaching a macroporous mesh suture to a standard-sized surgical needle, and a novel method of manufacturing such a medical device. Such macroporous mesh sutures have cross-sectional dimensions much larger than conventional mono-filament and solid braid type sutures, and prior to the present disclosure, there has been no need (and no solution) to attach such large macroporous mesh sutures to standard-sized surgical needles. Those skilled in the art realize that standard-sized suture needles are commonly in the range from 0.2 to 1.0 mm in cross-sectional diameter. For a standard drilled end needle, the internal void (e.g., blind bore) created by the drill for insertion of the suture will be less than the cross-sectional diameter of the needle. The present disclosure therefore provides a unique intervening segment (or segments) for indirectly effecting attachment of a mesh suture to a standard sized needle. This intervening segment effectively tapers and/or reduces the cross-sectional dimension of the macroporous mesh suture down to a manageable size for insertion into a conventional drilled needle or channeled needle, for example, or to a needle adapted to receive or otherwise join with the intervening segment. No such innovation has previously been deployed because no comparable macroporous mesh sutures existed.

DETAILED DESCRIPTION

Figures 1, 2, 3:
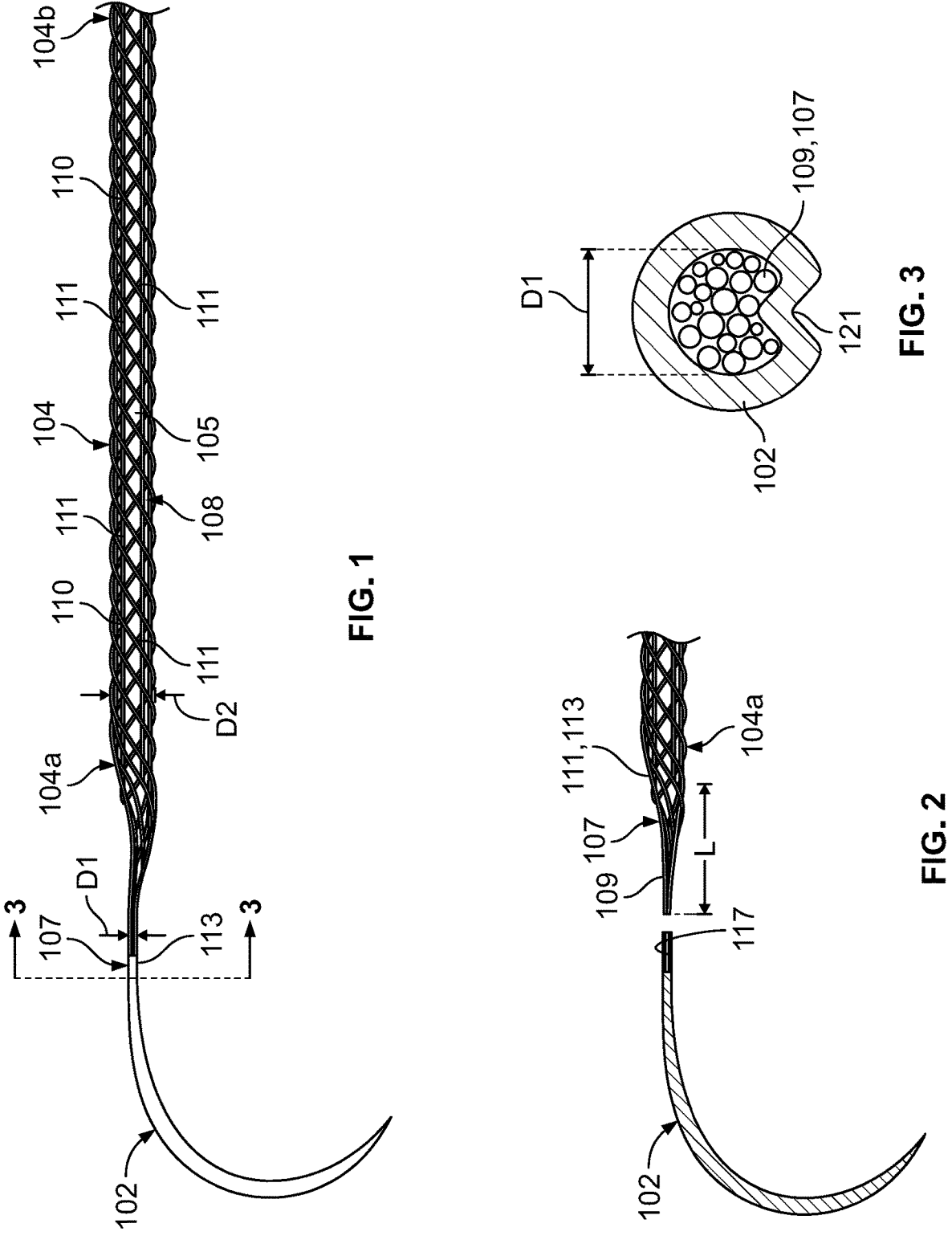
FIG. 1 is a perspective view of a medical device constructed in accordance with the present disclosure showing a mesh suture attached to a surgical needle via an intervening segment.
FIG. 2 is an exploded view of a portion of the surgical needle and mesh suture of FIG. 1 shown in cross-section.
FIG. 3 is a cross-sectional view of the medical device of FIG. 1 taken through line 3-3 of FIG. 1.

FIG. 1 depicts a medical device 100 that includes a surgical needle 102 and an elongated suture 104 attached to the surgical needle 102. The needle 102 can be contoured or curved needle with a flattened cross-sectional profile, but needles with generally any geometry could be used. The suture 104 has a first end 104a attached to the needle 102 and a second end 104b located a distance away from the needle 102. The length of the suture 104 in FIG. 1 is representative only, and in practice, the length could be any desirable length as discussed below. The suture 104 can include a plurality of individual fibers 111, only a few of which are identified in FIG. 1 for simplicity. The fibers 111 are braided, knitted, or otherwise woven, extruded, or fused together into a mesh construct defining a plurality of pores 110, which advantageously facilitate tissue incorporation, as will be discussed below.

In the depicted embodiment, the needle 102 is indirectly attached to the suture 104 by way of an intervening segment 107. The intervening segment 107 is disposed between the first end 104a of the elongated mesh suture 104 and the needle 102. In this version, the intervening segment 107 includes at least some of the plurality of fibers 111 converging from the first end 104a of the mesh suture 104 into a bundled configuration 113 having a cross-sectional dimension D1 that is smaller than a cross-sectional dimension D2 of the mesh suture 104. In one alternative version, the plurality of fibers 111 comprising the mesh suture 104 can include a single alpha fiber that is thicker than or stronger than all of the remaining fibers. In this instance, one version of the medical device 100 can include an intervening segment 107 that includes only the alpha fiber extending from the first end 104a of the suture 104, such that as the first end 104a of the mesh suture 104 transitions (e.g., tapers, converges, etc.) to the intervening segment 107, a length of the alpha fiber that then continues beyond to define the intervening segment 107 for attaching directly or indirectly to the needle 102 as discussed in more detail below.

In some versions, the cross-sectional dimension of the mesh suture 104 can be in a range of approximately 1 mm to approximately 10 mm, or even as large as approximately 25 mm. In some versions, the cross-sectional dimension of the intervening segment 107 can be in a range of approximately 0.1 mm to approximately 50 mm, and a length L (FIG. 2) of the intervening segment 107 can be in a range of approximately 0.5 mm to approximately 200 mm. For most uses, the cross-sectional dimension of the intervening segment 107 will be in a range of approximately 0.2 mm to approximately 20 mm, and a length L (FIG. 2) of the intervening segment 107 can be in a range of approximately 0.5 mm to approximately 50 mm.

In some versions, the cross-section of the intervening segment 107 can be generally circular such that the cross-sectional dimension D1 of the intervening segment will represent a diameter of the intervening segment 107. In some versions, the cross-section of the suture 104 will be either generally circular or generally flat (e.g., rectangular) such that the cross-sectional dimension D2 of the suture 104 will be either a diameter or a width dimension of the suture 104, as will be discussed more thoroughly below. In some embodiments, there can be multiple intervening segments 107 (either alone or in sequence) to indirectly attach either end of the suture 104 to the needle 102. In some versions, the intervening segment 107 includes only one of the plurality of fibers 111 converging from the first end 104a of the mesh suture 104 into configuration 113 having a cross-sectional dimension D1 that is smaller than a cross-sectional dimension D2 of the mesh suture 104. In some versions, a single filament indirectly attaches the needle 102 to the mesh suture 104, and in some versions a portion of the mesh suture fibers 111 join with a cross-sectional dimension to fit into the drill or channel end opposite the sharp point of the needle 102. In other versions, the single fiber or the portion of mesh suture fibers 111 that are indirectly attached to the needle 102 join with the longitudinal elements of the mesh suture 104 to limit roping.

With continued reference to FIG. 1, the plurality of fibers 111 taper from the larger cross-sectional dimension D2 at the first end 104a of the mesh suture 104 to the smaller cross-sectional dimension D1 in the bundled configuration 113. So configured, the bundled configuration 113 of the plurality of fibers 111 in the intervening segment 107 facilitate indirect attachment of the mesh suture to the surgical needle 102, which in the depicted version includes a drilled needle having a blind bore 117, as shown in FIGS. 2 and 3.

In some versions, the plurality of fibers 111 in the intervening segment 107 are fixed together in the bundled configuration 113 by way of heat annealing, welding, wrapping, staking, bonding, and/or adhering. Fixing the fibers together can help facilitate handling and attachment to the needle 102 by disposing a terminal end 109 of the intervening segment 107 into the blind bore 117, as seen in FIGS. 1 and 3. In other versions, the plurality of fibers 111 are not fixed together but join solely at the indirect attachment to the needle 102. In other versions, the fibers 111 in the intervening segment 107 can be held together by a sheath (not shown) made out of any type of material that is disposed or wrapped around the bundled configuration 113. For example, one sheath may include a plastic sheet of material wrapped tightly around the bundled configuration 113, an individual fiber wrapped multiple times around the bundled configuration 113 and tied off, a heat shrinkable rubber tube disposed about the bundled configuration 113, or some other means. In some versions, after the intervening segment 107 is inserted into the blind bore 117, that portion of the needle 102 may be worked with a tool, for example, to include a crimp 121 (shown in FIG. 3) that assists with retaining the intervening segment 107 in the blind bore 117. Alternatively, the indirect attachment can be achieved by having only a portion or minority of the filaments 111 reach the blind bore 107, with the other fibers joining within the intervening segment 107 to become the mesh suture 104*a*.

While the needle in FIGS. 1 and 2 has been described as including a drilled needle, in other versions, the needle can include a channeled needle or some other type of needle. With a channeled needle, the needle 102 would include an open elongated channel instead of the blind bore 117. Similarly though, the terminal end 109 of the intervening segment 107 would be inserted into the channel and the channel would be crimped to retain the intervening segment 107 in connection with the needle. With either drilled or channeled needles, it is also possible to incorporate additional or alternative retention means between the needle 102 and intervening segment 107 such as adhesive, welding, staking, swaging, etc. In other versions, the needle 102 can be a "French eye" needle where the mesh suture 104 or intervening segment 107 passes through a continuous or discontinuous loop formed by the end of the needle 102 opposite the sharp point.

As mentioned, the intervening segment 107 comprises a bundled configuration 113 of a plurality of fibers 111. In some versions, the plurality of fibers 111 in the intervening segment 107 can be braided together into a configuration with a smaller cross-section dimension D1 than the suture 104. Thus, the intervening segment 107 may include a tight braid to achieve this, or may include a loose braid with the fibers 111 collapsed onto themselves, or may include a sheath or casing of some type (not shown) In other versions, the plurality of fibers 111 can simply be aligned parallel together and in close contact with each other. Other configurations are possible. In these configurations, the intervening segment 107 is generally non-porous. In other versions, however, the intervening segment 107 could be microporous or nano-porous. And in any configuration, the intervening segment 107 could include surface texture defined by the external geometry of the plurality of fibers 111 bundled together, barbs, or adhesive chemical elements to draw the filaments towards each other.

As mentioned above, the mesh suture 104 of the present disclosure can include a tubular mesh suture, a flat mesh suture, or some other configuration of mesh suture. As shown in FIG. 1, one version of the mesh suture 104 can include a tubular wall 105 extending the entire length of the suture 104 between the first and second ends 104*a*, 104*b*. The tubular wall 105 defines a hollow core 108. In other versions, less than the entire length of the suture 104 can be tubular. For example, it is foreseeable that either or both of the first and second ends 14*a*, 14*b* can have a non-tubular portion or portion of other geometry. Such non-tubular portions could be for serving as an intervening segment (as discussed herein throughout) for attaching the first end 14*a* of the suture 14 to the needle 12, for tying off the second end 14*b*, or otherwise for example. In versions where the entire length of the suture 104 is tubular, as shown, the entire length of the suture 104 including the ends and central portion can also have a generally constant or uniform cross-sectional dimension D2, i.e., diameter or thickness, in the absence of stresses. That is, no portion of the suture 104 is meaningfully larger in diameter than any other portion of the suture 104. Moreover, no aspect, end, or other portion of the suture 104 is intended to be or is actually passed through, disposed in, received in, or otherwise positioned inside of the hollow core 108. The hollow core 108 is adapted for receiving tissue in-growth only. In other embodiments, substantially the entire suture 104 can be substantially flat or planar without a hollow core. In such versions, the suture 104 may include a single flat suture wall, and the cross-sectional dimension D2 can be a width of the flat suture wall which is greater than a thickness of the suture wall.

In some embodiments, the suture 104, whether tubular, flat, or otherwise, can have a length extending from the first end 104*a* to the second end 104*b* that is greater than or equal to approximately 20 cm, greater than or equal to approximately 30 cm, greater than or equal to approximately 40 cm, greater than or equal to approximately 50 cm, greater than or equal to approximately 60 cm, greater than or equal to approximately 70 cm, greater than or equal to approximately 80 cm, greater than or equal to approximately 90 cm, and/or greater than or equal to approximately 100 cm, or even bigger. In some embodiments of tubular sutures, the tubular wall 105 can have a diameter in a range of approximately 1 mm to approximately 10 mm, and even as big as 25 mm (2.5 cm). Moreover, in some embodiment, a flat suture can have a width in a range of approximately 1 mm to approximately 10 mm, and even as big as approximately 30 mm. Regardless of the shape, the suture 104 and also the intervening segment 107 of the version described above can be constructed of a material such as, for example, polyethylene terephthalate, nylon, polyolefin, polypropylene, silk, polymers p-dioxanone, co-polymer of p-dioxanone, ε-caprolactone, glycolide, L(−)-lactide, D(+)-lactide, meso-lactide, trimethylene carbonate, polydioxanone homopolymer, poly-4-hydroxybutyrate, fibers derived from spider silk, grapheme, stainless steel, surgical steel, titanium, aluminum, any other metals including metal alloys suitable for the intended purpose, and any combination(s) of the aforementioned materials.

So constructed, with tubular sutures 104, the tubular wall 105 of the suture 104 can be radially deformable such that it adopts a first cross-sectional profile in the absence of lateral stresses and a second cross-sectional profile in the presence of lateral stresses. For example, in the absence of lateral stresses, the tubular wall 105 and therefore the suture 104 depicted in FIG. 1, for example, can have a circular cross-sectional profile, thereby exhibiting radial symmetry. In the presence of a lateral stress, such a suture 104 could then exhibit a partially or wholly collapsed conformation. The stiffness of the materials may vary from a suture that completely collapses with lateral stress, to a suture that retains its original profile with lateral stress.

Figure 4:
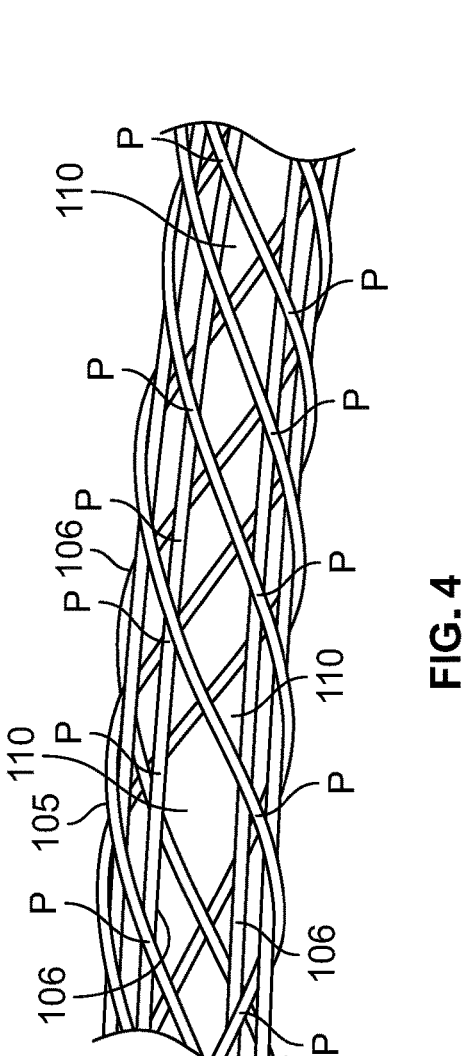
FIGS. 4 and 5 are detailed views of the mesh suture of FIG. 1.
Figure 6:
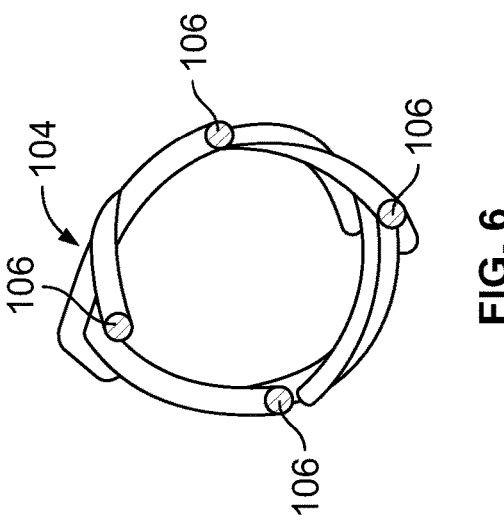
FIG. 6 is a cross-sectional view of the mesh wall of the suture of FIG. 1 taken through line 6-6 of FIG. 5.

As mentioned above, the suture 104 of FIG. 1 includes a mesh suture 104 defining a plurality of pores 110 for facilitating tissue incorporation through the mesh wall 105. As depicted in FIG. 4, in at least one version of the medical device 100, at least some of the wall 105, whether tubular, flat, or otherwise, can be macroporous defining the plurality of pores 110 (e.g., openings, apertures, holes, etc.), only a few of which are expressly identified by reference number and lead line in FIGS. 1 and 4 for clarity. The pores 110 extend completely through the mesh wall 105 and, in tubular versions, to the hollow core 108. In one version, the wall 105 can be constructed of a knitted, woven, or braided mesh material used in abdominal wall hernia repair.

As used herein, the term "macroporous" can include pore sizes that are at least greater than or equal to approximately 200 microns and, in some versions, greater than or equal to 500 microns. In some versions of the medical device 100, the size of at least some the pores 110 in the suture 104 can be in a range of approximately 500 microns to approximately 4 millimeters. In another version, at least some of the pores 110 can have a pore size in the range of approximately 500 microns to approximately 2.5 millimeters. In another version, at least some of the pores 110 can have a pore size in the range of approximately 1 millimeter to approximately 2.5 millimeters. In another version, the size of at least some of the pores 110 can be approximately 2 millimeters. More-over, in some versions, the pores 110 can vary in size. Some of the pores 110 can be macroporous (e.g., greater than approximately 200 microns) and some of the pores 110 can be microporous (e.g., less than approximately 200 microns). The presence of microporosity (i.e., pores less than approximately 200 microns) in such versions of the disclosed suture may only be incidental to the manufacturing process, which can including knitting, weaving, extruding, blow molding, or otherwise, but not necessarily intended for any other functional reason regarding biocompatibility or tissue inte-gration. The presence of microporosity (i.e. some pores less than approximately 200 microns in size) as a byproduct or incidental result of manufacturing does not change the character of the disclosed macroporous suture (e.g., with pores greater than approximately 200 microns, and prefer-ably greater than approximately 500 microns, for example), which facilitates tissue in-growth to aid biocompatibility, reduce tissue inflammation, and decrease suture pull-through.

In versions of the disclosed suture that has both macropo-rosity and microporosity, the number of pores 110 that are macroporous can be in a range from approximately 1% of the pores to approximately 99% of the pores (when mea-sured by pore cross-sectional area), in a range from approxi-mately 5% of the pores to approximately 99% of the pores (when measured by pore cross-sectional area), in a range from approximately 10% of the pores to approximately 99% of the pores (when measured by pore cross-sectional area), in a range from approximately 20% of the pores to approxi-mately 99% of the pores (when measured by pore cross-sectional area), in a range from approximately 30% of the pores to approximately 99% of the pores (when measured by pore cross-sectional area), in a range from approximately 50% of the pores to approximately 99% of the pores (when measured by pore cross-sectional area), in a range from approximately 60% of the pores to approximately 99% of the pores (when measured by pore cross-sectional area), in a range from approximately 70% of the pores to approxi-mately 99% of the pores (when measured by pore cross-sectional area), in a range from approximately 80% of the pores to approximately 99% of the pores (when measured by pore cross-sectional area), or in a range from approximately 90% of the pores to approximately 99% of the pores (when measured by pore cross-sectional area).

So configured, the pores 110 in the suture 104 are arranged and configured such that the suture 104 is adapted to facilitate and allow tissue in-growth and integration through the pores 110 in the mesh wall 105 when introduced into a body. That is, the pores 110 are of sufficient size to achieve maximum biocompatibility by promoting local/normal tissue in-growth through the pores 110 of the suture 104 and, with tubular sutures, into the hollow core 108. As such, tissue growth through the pores 110 enables the suture 104 and resultant tissue to combine and cooperatively increase the strength and efficacy of the medical device 100, while also decreasing irritation, inflammation, local tissue necrosis, and likelihood of pull through. Instead, the suture 14 promotes the production of healthy new tissue throughout the suture construct including inside the pores 110, and with tubular sutures 104, the hollow core 108.

While a tubular version of the suture 104 has been described as including a single elongated hollow core 108, in some embodiments, a suture according to the present disclosure can comprise a tubular wall defining a hollow core including one or more interior voids (e.g., extending the length of the suture). In some versions, at least some of the interior voids can have a size or diameter >approximately 200 microns, >approximately 300 microns, >approximately 400 microns, >approximately 500 microns, >approximately 600 microns, >approximately 700 microns, >approximately 800 microns, >approximately 900 microns, >approximately 1 millimeter, or >approximately 2 millimeters. In some embodiments, a suture according to the present disclosure can comprise a tubular wall defining a hollow core including one or more (e.g., 1, 2, 3, 4, 5, 6, 7, 8, or more) lumens (e.g., running the length of the suture). In some embodiments, a suture according to the present disclosure can comprise a tubular wall defining a hollow core including a honeycomb structure, a 3D lattice structure, or other suitable interior matrix, which defines one or more interior voids. In some versions, at least some of the interior voids in the honey-comb structure, 3D lattice structure, or other suitable matrix can have a size or diameter >approximately 200 microns, >approximately 300 microns, >approximately 400 microns, >approximately 500 microns, >approximately 600 microns, >approximately 700 microns, >approximately 800 microns, >approximately 900 microns, >approximately 1 millimeter, or >approximately 2 millimeters. In some embodiments, a void comprises a hollow core. In some embodiments, a hollow core can include a hollow cylindrical space in the tubular wall, but as described, the term "hollow core" is not limited to defining a cylindrical space, but rather could include a labyrinth of interior voids defined by a honeycomb structure, a 3D lattice structure, or some other suitable matrix. In some embodiments, sutures comprise a hollow, flexible structure that has a circular cross-sectional profile in its non-stressed state, but which collapses into a more flattened cross-sectional shape when pulled in an off-axis direction. In some embodiments, sutures are provided that exhibit radial symmetry in a non-stressed state. In some embodiments, radial symmetry in a non-stressed state elimi-nates the need for directional orientation while suturing. In some embodiments, sutures are provided that exhibit a flattened cross-sectional profile when off-axis (longitudinal axis) force is applied (e.g., tightening of the suture against tissue), thereby more evenly distributing the force applied by the suture on the tissue. In some embodiments, sutures are provided that exhibit a flattened cross-sectional profile when axial force is applied. In some embodiments, sutures comprise flexible structure that adopts a first cross-sectional profile in its non-stressed state (e.g., suturing profile), but adopts a second cross-sectional shape when pulled in an off-axis direction (e.g., tightened profile). In some embodi-ments, a suture is hollow and/or comprises one or more internal voids (e.g., that run the length of the suture). In some embodiments, internal voids are configured to encour-age the suture to adopt a preferred conformation (e.g., broadened leading edge to displace pressures across the contacted tissue) when in a stressed states (e.g., tightened profile). In some embodiments, internal voids are configured to allow a suture to adopt radial exterior symmetry (e.g., circular outer cross-sectional profile) when in a non-stressed state. In some embodiments, varying the size, shape, and/or placement of internal voids alters one or both of the first cross-sectional profile (e.g., non-stressed profile, suturing profile) and second cross-sectional profile (e.g., off-axis profile, stressed profile, tightened profile). In some embodi-ments, an internal element is absorbed over time, rendering the space confined by the outer mesh changing as to shape and size. In some elements, the space confined by the outer mesh is used to deliver cells or medicaments for delivery to the tissues.

Sutures, which are substantially linear in geometry, have two distinct ends, as described above with reference to FIG. 1, for example. In some embodiments, both ends are identical. In some embodiments, each end is different. In some embodiments, one or both ends are structurally unadorned. In some embodiments, the end away from the needle 102 is a free end, has a taper, is attached to a barb, is a loop, is attached to another needle directly or indirectly, or is attached indirectly to a planar mesh. In some embodiments, one or more ends is attached to or at least configured for attachment to a needle via swaging, sonic welding, adhesive, tying, or some other means (as shown FIG. 1). In some embodiments, the second end 104b of the suture 104 is configured to include an anchor for anchoring the suture 104 against the tissue through which the suture 104 is inserted. In some embodiments, the second end 104b of the suture 104 is configured to anchor the suture at the beginning of the closure. In some embodiments, the second end 104b of the suture 104 includes an anchor that is a structure that prevents the suture 104 from being pulled completely through the tissue. In some embodiments, the anchor has a greater dimension than the rest of the suture 104 (at least 10% greater, at least 25% greater, at least 50% greater, at least 2-fold greater, at least 3-fold greater, at least 4-fold greater, at least 5-fold greater, at least 6-fold greater, at least 10-fold greater, etc.). In some embodiments, the anchor comprises a structure with any suitable shape for preventing the suture 104 from being pulled through the hole (e.g., ball, disc, plate, cylinder), thereby preventing the suture 14 from being pulled through the insertion hole. In some embodiments, the anchor of the suture 104 comprises a closed loop. In some embodiments, the closed loop is of any suitable structure including, but not limited to a crimpled loop, flattened loop, or a formed loop. In some embodiments, a loop can be integrated into the end of the suture 104. In some embodiments, a separate loop structure can be attached to the suture 104. In some embodiments, the needle 102 can be passed through the closed loop anchor to create a cinch for anchoring the suture 104 to that point. In some embodiments, the anchor can comprise one or more structures (e.g., barb, hook, etc.) to hold the end of the suture 104 in place. In some embodiments, one or more anchor 22 structures (e.g., barb, hook, etc.) are used in conjunction with a closed loop to ratchet down the cinch and hold its position. In some embodiments, a knotless anchoring system can be provided. In some embodiments, a needle can be attached to the second end 104b to create a double armed suture. In some embodiments, a single mesh suture or multiple mesh sutures are attached through indirect attachments to a larger device such as a reconstruction mesh or implant to aid in deployment of the larger device.

In some embodiments, and as briefly mentioned relative to FIG. 1, the present disclosure provides suturing needles with cross-sectional profiles indirectly attached to a mesh suture via an intervening segment and configured to prevent suture pull-through and methods of use thereof. In some embodiments, suturing needles are provided comprising cross-section shapes (e.g. flat, elliptical, transitioning over the length of the needle, etc.) that reduce tension against the tissue at the puncture site and reduce the likelihood of tissue tear. In some embodiments, one cross-sectional dimension of the needle is greater than the orthogonal cross-sectional dimension (e.g., 1.1× greater, 1.2× greater, 1.3× greater, 1.4× greater, 1.5× greater, 1.6× greater, 1.7× greater, 1.8× greater, 1.9× greater, >2× greater, 2.0× greater, 2.1× greater, 2.2× greater, 2.3× greater, 2.4× greater, 2.5× greater, 2.6× greater, 2.7× greater, 2.8× greater, 2.9× greater, 3.0× greater, >3.0× greater, 3.1× greater, 3.2× greater, 3.3× greater, 3.4× greater, 3.5× greater, 3.6× greater, 3.7× greater, 3.8× greater, 3.9× greater, 4.0× greater, >4.0× greater . . . >5.0× greater . . . >6.0× greater . . . >7.0× greater . . . >8.0× greater . . . >9.0× greater . . . >10.0× greater). In some embodiments, suturing needles are provided circular in shape at its point (e.g., distal end), but transition to a flattened profile (e.g., ribbon-like) to the rear (e.g. proximal end). In some embodiments, the face of the flattened area is orthogonal to the radius of curvature of the needle. In some embodiments, suturing needles create a slit (or flat puncture) in the tissue as it is passed through, rather than a circle or point puncture. In some embodiments, suturing needles are provided circular in shape at its point (e.g., distal end), but transition to a 2D cross-sectional profile (e.g., ellipse, crescent, half moon, gibbous, etc.) to the rear (e.g. proximal end). In some embodiments, suturing needles provided herein find use with the sutures described herein. In some embodiments, suturing needles find use with sutures of the same shape and/or size. In some embodiments, suturing needles and sutures are not of the same size and/or shape. In some embodiments, suturing needles provided herein find use with traditional sutures. Various types of suture needles are well known in the art. In some embodiments, suturing needles provided herein comprise any suitable characteristics of suturing needles known to the field, but modified with dimensions described herein. Any introduction device of the mesh suture through tissue is defined as a needle, and therefore we do not limit our embodiments to those defined here, but rather any sharp instrument that can penetrate tissue to pass the suture.

In some embodiments, the present disclosure also provides compositions, methods, and devices for anchoring the suture at the end of the closure (e.g., without tying the suture to itself). In some embodiments, one or more securing elements (e.g., staples) are positioned over the terminal end of the suture to secure the end of the closure. In some embodiments, one or more securing elements (e.g., staples) are secured to the last "rung" of the suture closure (e.g., to hold the suture tight across the closure). In some embodiments, a securing element is a staple. In some embodiments, a staple comprises stainless steel or any other suitable material. In some embodiments, a staple comprises a plurality of pins that can pass full thickness through 2 layers of suture. In some embodiments, staple pins are configured to secure the suture end without cutting and/or weakening the suture filament. In some embodiments, a staple forms a strong joint with the suture. In some embodiments, a staple is delivered after the needle is cut from the suture. In some embodiments, a staple is delivered and the needle removed simultaneously In some embodiments, the present disclosure provides devices (e.g., staple guns) for delivery of a staple into tissue to secure the suture end. In some embodiments, a staple deployment device simultaneously or near-simultaneously delivers a staple and removes the needle from the suture. In some embodiments, a staple deployment device comprises a bottom lip or shelf to pass under the last rung of suture (e.g., between the suture and tissue surface) against which the pins of the staple can be deformed into their locked position. In some embodiments, the bottom lip of the staple deployment device is placed under the last rung of suture, the free tail of the suture is placed within the stapling mechanism, and the suture is pulled tight. In some embodiments, while holding tension, the staple deployment device is activated, thereby joining the two layers of suture together. In some embodiments, the device also cuts off the excess length of the free suture tail. In some embodiments, the staple deployment device completes the running suture and trims the excess suture in one step. In some embodiments, a suture is secured without the need for knot tying. In some embodiments, only 1 staple is needed per closure. In some embodiments, a standard stapler is used to apply staples and secure the suture end. In some embodiments, a staple is applied to the suture end manually. The staple may or may not have tissue integrative properties.

In some embodiments, sutures provided herein provide tissue integrative properties to increase the overall strength of the repair (e.g., at an earlier time-point than traditional sutures). In some embodiments, sutures are provided with enhanced tissue adhesion properties. In some embodiments sutures are provided that integrate with the surrounding tissue. In some embodiments, tissue integrative properties find use in conjunction with any other suture characteristics described herein. In some embodiments, sutures allow integration of healing tissue into the suture. In some embodiments, tissue growth into tubular sutures and/or through flat sutures is promoted (e.g., by the surface texture of the suture). In some embodiments, tissue growth into the suture prevents sliding of tissue around suture, and/or minimizes micromotion between suture and tissue. In some embodiments, tissue in-growth into tubular sutures and/or through flat sutures increases the overall strength of the repair by multiplying the surface area for scar in establishing continuity between tissues. Conventionally, the strength of a repair is dependent only on the interface between the two tissue surfaces being approximated. In some embodiments in-growth of tissue into the suture adds to the surface area of the repair, thereby enhancing its strength. In some embodiments, increasing the surface area for scar formation, the closure reaches significant strength more quickly, narrowing the window of significant risk of dehiscence.

In some embodiments, the surface and/or internal texture of a suture promotes tissue adhesion and/or ingrowth. In some embodiments, as discussed above specifically with reference to FIG. 1, a suture of the present disclosure can comprise a porous (e.g., macroporous) and/or textured material. In some embodiments, a suture comprises a porous (e.g., macroporous) and/or textured exterior. In some embodiments, pores in the suture allow tissue in-growth and/or integration. In some embodiments, a suture comprises a porous ribbon-like structure, instead of a tubular like structure. In some embodiments, a porous suture comprises a 2D cross-sectional profile (e.g., elliptical, circular (e.g., collapsible circle), half moon, crescent, concave ribbon, etc.). In some embodiments, a porous suture comprises polypropylene or any other suitable suture material as discussed above. In some embodiments, pores are between 500 µm and 3.5 mm or greater in diameter (e.g., e.g., >500 µm in diameter (e.g., >500 µm, >600 µm, >700 µm, 800 µm, >900 µm, >1 mm, or more). In some embodiments pores are of varying sizes. In some embodiments, a suture comprises any surface texture suitable to promote tissue in-growth and/or adhesion. In some embodiments, suitable surface textures include, but are not limited to ribbing, webbing, mesh, barbs, barbs with different directions or geometries, grooves, etc. In some embodiments, the suture may include filaments or other structures (e.g., to provide increased surface area and/or increased stability of suture within tissue). In some embodiments, interconnected porous architecture is provided, in which pore size, porosity, pore shape and/or pore alignment facilitates tissue in-growth.

In some embodiments, a suture comprises a mesh and/or mesh-like exterior. In some embodiments, a mesh exterior provides a flexible suture that spreads pressure across the closure site, and allows for significant tissue in-growth. In some embodiments, the density of the mesh is tailored to obtain desired flexibility, elasticity, and in-growth characteristics.

In some embodiments, a suture is coated and/or embedded with materials to promote tissue ingrowth. Examples of biologically active compounds that may be used sutures to promote tissue ingrowth include, but are not limited to, cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, laminin and other extracellular matrices, tissue inductive scaffolds, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-$\beta$, etc. Examples of pharmaceutically active compounds that may be used to promote tissue ingrowth include, but are not limited to, acyclovir, cephradine, malfalen, procaine, ephedrine, adriomycin, daunomycin, plumbagin, atropine, quanine, digoxin, quinidine, biologically active peptides, chlorin e.sub.6, cephalothin, proline and proline analogues such as cis-hydroxy-L-proline, penicillin V, aspirin, ibuprofen, steroids, antimetabolites, immunomodulators, nicotinic acid, chemodeoxycholic acid, chlorambucil, and the like. Therapeutically effective dosages may be determined by either in vitro or in vivo methods.

Sutures are well known medical devices in the art. In some embodiments, sutures have braided or monofilament constructions. In some embodiments sutures are provided in single-armed or double-armed configurations with a surgical needle mounted to one or both ends of the suture, or may be provided without surgical needles mounted. In some embodiments, the end of the suture distal to the needle comprises one or more structures to anchor the suture. In some embodiments, the distal end of the suture comprises one or more of a: closed loop, open loop, anchor point, barb, hook, etc. In some embodiments, sutures comprise one or more biocompatible materials. In some embodiments, sutures comprise one or more of a variety of known bioabsorbable and nonabsorbable materials. For example, in some embodiments, sutures comprise one or more aromatic polyesters such as polyethylene terephthalate, nylons such as nylon 6 and nylon 66, polyolefins such as polypropylene, silk, and other nonabsorbable polymers. In some embodiments, sutures comprise one or more polymers and/or copolymers of p-dioxanone (also known as 1,4-dioxane-2-one), ε-caprolactone, glycolide, L(–)-lactide, D(+)-lactide, mesolactide, poly-4-hydroxybutyrate, trimethylene carbonate, fibers derived from spider silk, graphene, and combinations thereof. In some embodiments, sutures comprise polydioxanone homopolymer. The above listing of suture materials should not be viewed as limiting. In some embodiments, the disclosed sutures can be constructed of metal filaments such as stainless steel filaments. Suture materials and characteristics are known in the art. Any suitable suture materials or combinations thereof are within the scope of the present disclosure. In some embodiments, sutures comprise sterile, medical grade, surgical grade, and or biodegradable materials. In some embodiments, a suture is coated with, contains, and/or elutes one or more bioactive substances (e.g., antiseptic, antibiotic, anesthetic, promoter of healing, etc.).

In some embodiments, the suture filaments and/or the hollow core 108 of any of the disclosed sutures can contain a drug product for delivery to the patient, the medicament could take the form of a solid, a gel, a liquid, or otherwise. In some embodiments, the suture filaments and/or the hollow core 108 of any of the disclosed sutures can be seeded with cells or stem cells to promote healing, ingrowth or tissue apposition.

In some embodiments, the structure and material of the suture provides physiologically-tuned elasticity. In some embodiments, a suture of appropriate elasticity is selected for a tissue. In some embodiments, suture elasticity is matched to a tissue. For example, in some embodiments, sutures for use in abdominal wall closure will have similar elasticity to the abdominal wall, so as to reversibly deform along with the abdominal wall, rather than act as a relatively rigid structure that would carry higher risk of pull-through. In some embodiments, elasticity would not be so great however, so as to form a loose closure that could easily be pulled apart. In some embodiments, deformation of the suture would start occurring just before the elastic limit of its surrounding tissue, e.g., before the tissue starts tearing or irreversibly deforming.

In some embodiments, sutures described herein provide a suitable replacement or alternative for surgical repair meshes (e.g., those used in hernia repair). In some embodiments, the use of sutures in place of mesh reduces the amount of foreign material placed into a subject. In some embodiments, the decreased likelihood of suture pull-through allows the use of sutures to close tissues not possible with traditional sutures (e.g., areas of poor tissue quality (e.g., muscle tissue lacking fascia, friable or weak tissue) due to conditions like inflammation, fibrosis, atrophy, denervation, congenital disorders, attenuation due to age, or other acute and chronic diseases). Like a surgical mesh, sutures described herein permit a distribution of forces greater than that achieved by standard sutures delocalizing forces felt by the tissue and reducing the chance of suture pull-though and failure of the closure.

In some embodiments, sutures are permanent, removable, or absorbable. In some embodiments, permanent sutures provide added strength to a closure or other region of the body, without the expectation that the sutures will be removed upon the tissue obtaining sufficient strength. In such embodiments, materials are selected that pose little risk of long-term residency in a tissue or body. In some embodiments, removable sutures are stable (e.g., do not readily degrade in a physiological environment), and are intended for removal when the surrounding tissue reaches full closure strength. In some embodiments, absorbable sutures integrate with the tissue in the same manner as permanent or removable sutures, but eventually (e.g., >1 week, >2 weeks, >3 weeks, >4 weeks, >10 weeks, >25 weeks, >1 year) biodegrade and/or are absorbed into the tissue after having served the utility of holding the tissue together during the post-operative and/or healing period. In some embodiments absorbable sutures present a reduced foreign body risk.

Although prevention of dehiscence of abdominal closures (e.g., hernia formation) is specifically described at an application of embodiments of the present disclosure, the sutures described herein are useful for joining any tissue types throughout the body. In some embodiments, sutures described herein are of particular utility to closures that are subject to tension and/or for which cheese-wiring is a concern. Exemplary tissues within which the present disclosure finds use include, but are not limited to: connective tissue, fascia, ligaments, muscle, dermal tissue, cartilage, tendon, or any other soft tissues. Exemplary tissues also include bone. Specific applications of sutures described herein include reattachments, plication, suspensions, slings, etc. Sutures described herein find use in surgical procedures, obstetrics and cervical cerclage, non-surgical medical procedures, veterinary procedures, in-field medical procedures, etc. The scope of the present disclosure is not limited by the potential applications of the sutures described herein.

One method of manufacturing a medical device in accordance with the present disclosure can include forming a plurality of fibers 111 into a tubular mesh suture 104 with a tubular wall 105 having a plurality or pores 110 and defining a hollow core 108, each pore 110 having a pore size that is greater than 200 microns. In some version, this can include braiding or knitted the fibers 111 together around a mandrel, for example, and then subsequently removing the mandrel. In some versions, the fibers 111 may be fixed together where they cross or intersect each other. This fixation may include applying an adhesive, staking, heating, compressing, welding the fibers 111 together, or otherwise. This fixation may occur before or after the mandrel is removed.

Additionally, the method of manufacturing can include directly attaching either the first end 104*a* or the second end 104*b*, or even both ends of the mesh suture 104 to the surgical needle 102. Attaching the suture 104 to the needle 102 may also include forming the intervening segment 107, and then attaching the intervening segment 107 to the needle 102 such that the suture 104 is indirectly attached to the needle 102. As discussed above, in one version, forming the intervening segment 107 can include collecting at least some of the plurality of fibers 111 extending from the first end 104*a* of the mesh suture 104 and arranging them in a bundled configuration 113 that has a cross-sectional dimension D1 smaller than a cross-sectional dimension D2 of the suture 104. In some versions, this includes braiding, bonding, compressing, adhering, or knitting the plurality of fibers 111 into the bundled configuration 113. In some other versions, this can include arranging the plurality of fibers 111 parallel to each other and in contact with each other with or without the use of a cap, cover, or sheath to contain and compress the fibers down to the size of a conventional surgical needle for purposes of attachment. In other versions, a minority of fibers or even a single fiber are manufactured to reach the needle indirectly.

Finally, forming the intervening segment 107 includes fixing the plurality of fibers 111 in the bundled configuration 113 together, as mentioned above. This can be achieved by applying heat to secure the fibers 111 together, applying adhesive to adhere the fibers 111 together, applying energy (e.g., sonic energy, laser energy, etc.) to weld the fibers 111 together, staking the fibers 111 together, compressing the fibers 111 together with pressure, or some other process alone or in combination with the above. In still other methods, forming the intervening segment 107 can include placing a cap or cover, wrapping a plastic sheet, shrinking a rubber tube, or tying an individual filament around the fibers 111 to maintain the bundled configuration 113.

With the intervening segment 107 formed, the terminal end 109 can be inserted into the blind bore 117 of the needle 102 and the needle 102 can optionally be crimped. In some versions, a further or alternative step of fixing the intervening segment 107 into the blind bore 109 with an adhesive, or some other process such as welding, bonding, staking, etc., can be performed. In other versions where the needle 102 includes a channeled needle, the step of attaching the needle 102 to the intervening segment 107 of course includes at least disposing the terminal end 109 in the channel and crimping the channel.

As discussed, forming the tubular wall 105 can include forming a tube from a mesh material. The tubular mesh wall 105 may be formed by directly weaving, braiding, or knitting fibers into a tube shape. Alternatively, forming the tubular mesh wall 16 can include weaving, braiding, or knitting fibers into a planar sheet and subsequently forming the planar sheet into a tube or flat shape. Finally, as mentioned throughout, forming the mesh suture 104 can include forming a flat planar mesh wall, instead of a tubular mesh wall 105. In this configuration, the same steps as those stated above would similarly apply with the exception of using a mandrel to form the tube. Instead, the flat planar mesh wall would simply be braided, knitted, or otherwise formed or even cut from a larger sheet of pre-formed mesh. Of course, other manufacturing possibilities including extrusion exist and manipulating a plurality of fibers is not the only possibility for creating a porous mesh wall within the scope of the present disclosure, but rather, are mere examples.

Still further, a method of manufacturing a medical device 100 in accordance with the present disclosure can include providing an anchor on the second end 104b of the wall 105 opposite the needle 102. In some versions of the method, and as one example only, providing the anchor can be as simple as forming a loop.

In some embodiments, the mesh wall 105 can be divided into two or more mesh wall portions by one or more intervening features such as knots, inflexible rod-like members, monofilament or multi-filament suture segments, etc. Such a construct can be referred to as a segmented mesh suture constructed in accordance with the present disclosure.

Figure 5:
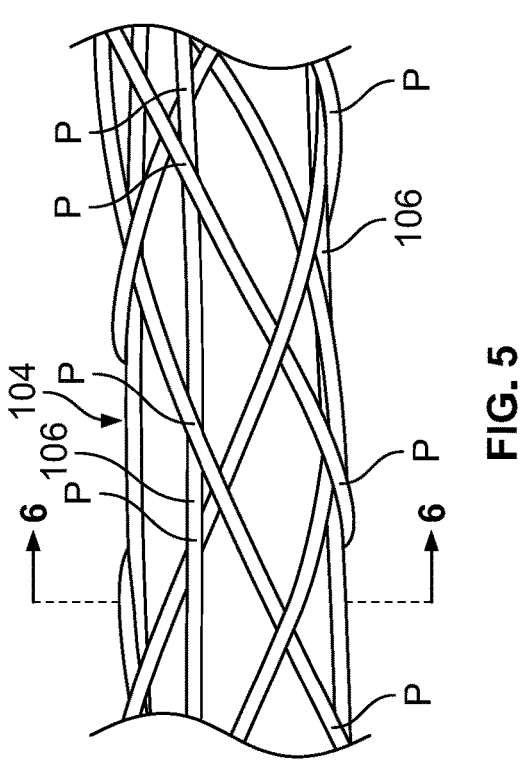

One optional feature of the medical device 100 of FIGS. 1-6 is that it can include one or more anti-roping elements 106, which are best seen in FIG. 4. That is, the medical device 100 can include one or more, or a plurality of, anti-roping elements 106 in the form of elongated elements 106 extending substantially (or entirely) the entire length of the suture 104 between the first and second ends 104a, 104b. The elongated elements 106 are fixed (or are not fixed) to the mesh wall 105 of the suture 104 at a plurality of points P and thereby serve to resist elongation of the suture 104 upon the application of an axial tensile load to the medical device 100. In some embodiments, the elongated elements 106 can be fixed to the mesh wall 105 in any available manner including, without limitation, welding, gluing, tying, braiding, heating, staking, dipping, chemically bonding, etc. In some embodiments, the elongated elements 106 are not fixed to the individual fibers of a tubular mesh walled suture 104. In some embodiments, the various fibers that make up the mesh wall 105 of any of the sutures described herein can also be fixed together at the intersection between fibers/filaments in any available manner including, without limitation, welding, gluing, tying, braiding, heating, staking, dipping, chemically bonding, etc. As shown in FIG. 5 illustrating a tubular suture 104, for example, the present version of the anti-roping elements 106 can be arranged such that each anti-roping element 106 is interleaved between adjacent elements of the remainder of the mesh suture 104, which can add to the integrity and stability of the suture 104. In other embodiments, the anti-roping elements 106 can be positioned entirely on an outer perimeter or on an inner perimeter of the tubular suture 104. In other embodiments, some of the elements 106 can be positioned on an inner perimeter, some can be positioned on an outer perimeter, and/or some can be interleaved such as depicted in FIG. 5. In other embodiments, some or all of the anti-roping elements may reside in the central core of a tubular mesh suture 104. In some embodiments, the anti-roping elements themselves are not entirely linear single filaments, but rather are a braid of fine filaments that act to run the length of the suture either obliquely or in step-wise fashion to resist elongation.

As mentioned above, "roping" is a phenomenon in the weaving industry whereby woven, braided, or knitted mesh materials tend to elongate under tension. This elongation can cause the various elements that make up the mesh material to collapse relative to each other and thereby reduce (e.g., close) the size of the pores disposed in the mesh. As such, the "anti-roping" elements 106 of the present disclosure, which are embodied as longitudinal elements in FIGS. 1-6, advantageously resist this elongation of the mesh suture and collapsing of the pores when the suture experiences axial tensile loads. This resistance is achieved because the anti-roping elements adds structural integrity to the overall construct and prevents the various mesh elements from moving relative to each other and/or deforming under tension. By maintaining the desired structural configuration of the mesh suture during and after threading into soft tissue, the pores remain appropriately sized to facilitate tissue integration and the overall width and/or dimension of the suture remains appropriately sized to limit and/or prevent suture pull through. These anti-roping elements may or may not continue and form the indirect attachment to the needle.

In FIGS. 1-6, the anti-roping elements 106 are each substantially straight (aka, substantially linear). In other embodiments, however, one or more the anti-roping elements 106 could foreseeably have different shapes, including for example, S-shaped, U-shaped, Zig-zag shaped, etc. Additionally, in FIGS. 1-6, each of the anti-roping elements 106 is a separate element. But, in other embodiments, any two or more of the elements 106 can be connected such that a single element 106 may extend the length of the suture 104, then include a U-shaped turn, and extend back along the length of the suture 104 adjacent to (e.g., parallel to) the preceding length. Also, in FIGS. 1-6, the anti-roping elements 106 are disposed parallel to each other and are equally spaced apart from each other. In alternative versions, the anti-roping elements 106 could have unequal spacing and/or could be disposed in a non-parallel manner. Further still, in FIGS. 1-6, the anti-roping elements 106 are depicted as having a thickness that is generally the same as the thickness of the other elements forming the mesh construct of the elongated suture 104. In other embodiments, any one or more of the anti-roping elements 106 could be thicker or thinner than the other elements forming the mesh construct of the elongated suture 104. Further yet, while FIGS. 1-6 show four (4) anti-roping elements, alternative embodiments could include any number so long as the desired objective is achieved without compromising or detracting from the macroporous character of the suture 104. Finally, while FIGS. 1-6 illustrate a hollow tubular suture 104, other embodiments of the medical device 100 as mentioned could include other geometries including, for example, a planar (e.g., flat ribbon) geometry. Therefore, it can be understood based on the foregoing description that the anti-roping elements 106 on such planar sutures 104 could include a plurality of substantially straight elements extending the length of the suture 104, and being parallel to each other and equally spaced apart. Alternatively, the anti-roping elements 106 on the planar suture 104 could take on any of the alternative constructs discussed with respect to the tubular construct expressly depicted in FIGS. 1-6.

As mentioned throughout the foregoing, some embodiments of the mesh wall 105 of the suture 104 of the present disclosure can be flat as opposed to tubular in construction. The foundational mesh of a flat suture 104 can be constructed in a manner similar to the foundational mesh of the tubular versions described above. For example, one method of manufacturing a flat suture 104 includes manufacturing a flat mesh wall 105 by weaving, braiding, or knitting fibers into a flat wall shape having some predefined width and length dimension. Alternatively, forming the flat mesh wall 105 can include weaving, braiding, or knitting fibers into a planar mesh sheet and subsequently cutting the planar sheet into strips.

Throughout the foregoing description, the medical device 100 of the present disclosure has been mostly described as including a mesh suture 104, a needle 102, and a single intervening segment 107. In other versions, the medical device 100 can include a plurality of intervening segments.

Figures 7, 8:
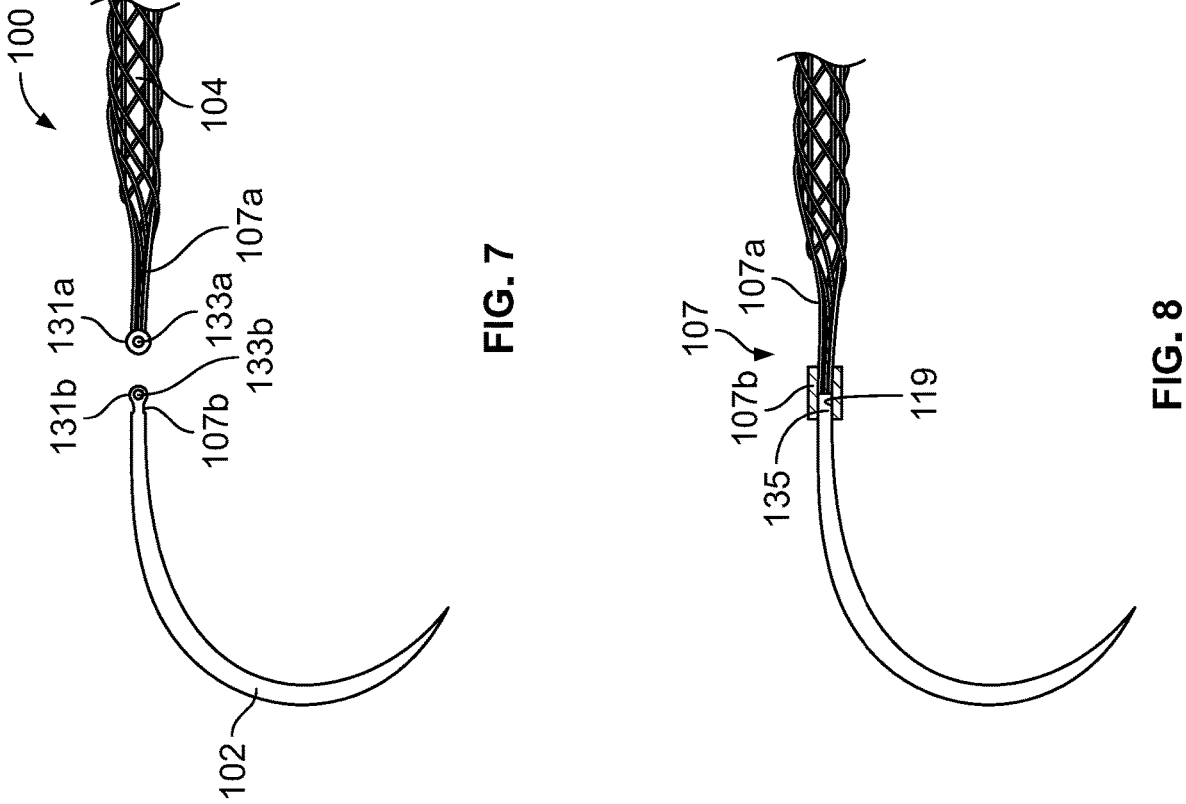
FIG. 7 is a partial exploded view of an alternative medical device constructed in accordance with the principles of the present disclosure.
FIG. 8 is a partial cross-sectional detail view of another alternative medical device constructed in accordance with the principles of the present disclosure.

For example, FIG. 7 depicts a detail view of one alternative medical device 100 including a mesh suture 104, needle 102, and first and second intervening segments 107a, 107b. The first intervening segment 107a is at least partially formed as part of the mesh suture 104 in a manner similar to the intervening segment 107 described throughout the present disclosure. The second intervening segment 107b is formed as the distal part of the needle 102. So configured, the first and second intervening segments 107a, 107b are adapted to be connected together to attach the needle 102 to the suture 104. More specifically, in the version depicted in FIG. 7, the first intervening segment 107a includes a male locking feature 131a disposed on a terminal end 119 of the intervening segment 107, and the second intervening segment 107b includes a female locking feature 131b. The male and female locking features 131a, 131b are each constructed of any relatively rigid biocompatible material. That is, in some versions, the male locking feature 131a has a locking protrusion 133a and can be constructed of a plastic component welded, swaged, or otherwise fixed to the terminal end 119 of the first intervening segment 107a, and the female locking feature 131b has a locking aperture 133b and can be formed as part of the metal material of the needle 102. To attach the needle 102 to the suture 104, the locking protrusion 133a of the male locking feature 131a is simply snap-fit into the locking aperture 133b of the female locking feature 131b. The features 131a, 131b can be retained together with friction, mechanical interlock, adhesive, magnetic elements, ball and socket, compression fit, or otherwise. Note that in some embodiments, the inter-positioning of the male and female intervening segments described above can also be reversed such that the male and female locking protrusion and aperture features are opposite to that described above.

Likewise, while the means for connecting the intervening segment 107 to the needle 102 has included either inserting a portion of the intervening segment 107 into the blind bore 117 or into a channel (not shown) formed in the needle 102, other versions of intervening segment arrangements are also contemplated. For example, FIG. 8 depicts an alternative version where the intervening segment 107 includes first and second sequentially or serially arranged intervening segments 107a, 107b, where the second intervening segment 107b (shown in cross-section in FIG. 8) includes a cylindrical collar defining a female bore or channel 119 and the needle 102 includes a male protrusion 135 that is disposed in the female bore or channel 119. The first intervening segment 107b in FIG. 8 is essentially the same as those described above in reference to FIGS. 1-6. In FIG. 8, the first intervening segment 107a and the male protrusion 135 of the needle 102 can be secured into the blind bore or channel 119 of the second intervening segment 107b in any manner mentioned hereinabove relative to the intervening segment 107 and needle 102 in FIGS. 1-6. As described above, in some embodiments, the inter-positioning of these male and female protrusions and channels or bores of the intervening segments described above can be reversed such that the male and female protrusion and channel or bore features are opposite to that described above. In some embodiments, both male to male and female to female intervening segment attachments are also contemplated, such as by the use of adhesive or other commonly known joining or bonding methods.

Although the disclosure has been described in connection with specific preferred embodiments, it should be understood that the disclosure as claimed should not be unduly limited to such specific embodiments. Indeed, various modifications of the described modes for carrying out the disclosure would be apparent to those skilled in the relevant fields are intended to be within the scope of the present disclosure. For example, and importantly, although the application includes discrete descriptions of different embodiments of the invention, it can be understood that any features from one embodiment can be easily incorporated into any one or more of the other embodiments.

I claim:

1. A medical device comprising:
a mesh suture having a first end and a second end located away from the first end, the mesh suture including a porous flat strip including a plurality of fibers extending between the first end and the second end, at least one fiber of the plurality of fibers being configured to attach a surgical needle to the first end of the mesh suture, and a plurality of pores extending through the porous flat strip, the plurality of pores including pores in a size range of 200 microns to 4 millimeters, the pores being adapted to facilitate tissue integration through the porous flat strip when the mesh suture is configured to be introduced into a body.

2. The medical device of claim 1, further comprising:
the surgical needle attached to the first end of the mesh suture.

3. The medical device of claim 2, further comprising:
the surgical needle attached to the second end of the mesh suture.

4. The medical device of claim 2, further comprising:
an intervening segment disposed between and connected to the first end of the mesh suture and the surgical needle.

5. The medical device of claim 4, wherein the intervening segment comprises one or more fibers of the plurality of fibers extending from the first end of the mesh suture and has a cross-sectional dimension that is smaller than a width of the mesh suture.

6. The medical device of claim 4, wherein the intervening segment comprises more than one of the plurality of fibers converging into a bundled configuration.

7. The medical device of claim 4, wherein the intervening segment is non-porous.

8. The medical device of claim 2, further comprising:
multiple intervening segments disposed between the first end of the mesh suture and the surgical needle, the multiple intervening segments being connected together to attach the surgical needle to the first end of the mesh suture.

9. The medical device of claim 1, wherein the mesh suture is constructed of a material selected from the group consisting of: polyethylene terephthalate, nylon, polyolefin, polypropylene, silk, polymers p-dioxanone, co-polymer of p-dioxanone, ε-caprolactone, glycolide, L(−)-lactide, D(+)-lactide, meso-lactide, trimethylene carbonate, polydioxanone homopolymer, metal fibers, poly-4-hydroxybutyrate, steel, titanium, fibers derived from spider silk, graphene, and combinations thereof.

10. The medical device of claim 1, wherein the mesh suture is at least 20 centimeters in length.

11. The medical device of claim 1, wherein the porous flat strip has a width from 3 millimeters to 40 millimeters.

12. The medical device of claim 1, wherein the porous flat strip extends the entire length of the mesh suture.

13. The medical device of claim 1, wherein the plurality of fibers are braided, knitted, woven, extruded, or fused together.

14. The medical device of claim 1, further comprising:

the surgical needle attached to the first end of the mesh suture; and a non-porous intervening segment disposed between the surgical needle and the first end of the mesh suture, the intervening segment comprising one or more fibers of the plurality of fibers extending from the first end of the mesh suture and having a cross-sectional dimension that is smaller than a width of the mesh suture, the mesh suture being constructed of a material selected from the group consisting of: polyethylene terephthalate, nylon, polyolefin, polypropylene, silk, polymers p-dioxanone, co-polymer of p-dioxanone, ε-caprolactone, glycolide, L(−)-lactide, D(+)-lactide, meso-lactide, trimethylene carbonate, polydioxanone homopolymer, metal fibers, poly-4-hydroxybutyrate, steel, titanium, fibers derived from spider silk, graphene, and combinations thereof, the mesh suture being at least 20 centimeters in length, the porous flat strip having a width from 3 millimeters to 40 millimeters and extending the entire length of the mesh suture, and the plurality of fibers being braided, knitted, woven, extruded, or fused together.

\* \* \* \* \*